US005945112A

United States Patent [19]
Flynn et al.

[11] Patent Number: 5,945,112
[45] Date of Patent: *Aug. 31, 1999

[54] METHOD FOR CUSTOMIZING DERMATOLOGICAL FOUNDATION PRODUCTS

[75] Inventors: Madeline Demayo Flynn, Monroe, Conn.; Richard Tyson Rigg, Springfield Gardens, N.Y.; Jason Oliver Hendry, Cheshire, Conn.

[73] Assignee: Elizabeth Arden Company, Division of Conopco, Inc., New York, N.Y.

[ * ] Notice: This patent is subject to a terminal disclaimer.

[21] Appl. No.: 09/033,176

[22] Filed: Mar. 2, 1998

Related U.S. Application Data

[63] Continuation-in-part of application No. 08/820,516, Mar. 19, 1997, Pat. No. 5,785,960.
[51] Int. Cl.⁶ .................................. A61K 6/00; A61K 7/00
[52] U.S. Cl. ................................................ 424/401; 424/63
[58] Field of Search ........................................ 424/401, 63

[56] References Cited

U.S. PATENT DOCUMENTS

| | | | |
|---|---|---|---|
| 4,871,262 | 10/1989 | Krauss et al. | 366/160 |
| 5,622,692 | 4/1997 | Rigg et al. | 424/63 |

FOREIGN PATENT DOCUMENTS 41 10 299   3/1991   Germany .

*Primary Examiner*—Johann Richter
*Assistant Examiner*—Sharon Howard
*Attorney, Agent, or Firm*—Milton L. Honig

[57] ABSTRACT

A method is provided for obtaining a customized skin foundation product to cover human skin imperfections. The steps include spectrophometrically measuring a customer's normal skin to obtain normal skin coloration values of lightness, redness and yellowness respectively denoted as L, a and b units. Thereafter the normal skin coloration values are converted through calculation to a modified value determined by a set program correcting L, a and b values. Based on the modified value the next step is formulating a facial foundation having color pursuant to the modified value. Adjustments are provided for redness and yellowness according to a set of schedules determined by the b/a ratio. Normally the measurement and skin imperfection determination are performed by a licensed dermatologist. Formulation and adjustment is is conducted at a site remote from the dermatologist office or place where the customer is measured and evaluated. Most preferred is the use of a formulation machine at the remote location to convert instructions received about a customer's modified formulation to dose and blend a series of cosmetic chemical compositions containing various monochromatic colors and skin benefit agents. The optimal formula dosed from the machine is packaged and then shipped to the customer.

14 Claims, No Drawings

METHOD FOR CUSTOMIZING DERMATOLOGICAL FOUNDATION PRODUCTS

This application is a continuation-in-part of application Ser. No. 08/820,516, Mar. 19, 1997, now U.S. Pat. No. 5,785,960.

BACKGROUND OF THE INVENTION

1. Field of the Invention

The invention concerns a method for customizing skin foundation products at a central location away from a remote customer.

2. The Related Art

There are many reasons why consumers wish to purchase skin foundation products in private as opposed to the public spaces of retail counters. For example, patients seeking the medical advice of dermatologists for the treatment of skin defects often experience underlying emotional consequences. Frequently, once the defect, such as acne, burn tissue or eczema has been treated, the healthy skin may appear blotched, mottled, scarred or uneven in texture or color. Healthy skin may also exhibit rosacea (skin 1 redness) or birth marks (port wine stains) regardless of the age or sex of the patient.

Skin discolorations have been generally left to the patient to address by seeking help at a cosmetics counter or aisle. Even if the customer gets past the embarrassment often associated with such public assistance, the selected product is often inappropriate for the skin type and need of the customer.

Cosmetic customers have been aided by a number of companies in the industry who have sought to provide a means for selecting the customer's optimal color shade. For example, Clinique and Clarion have installed computers at sales counters for use by the customer. Information on color shade, oiliness and other properties of a customer's skin are punched into the computer which then determines the company's most closely matching product.

Custom blending is also offered by two major companies, Prescriptives (division of Estee Lauder) and Visage (division of Revlon). They begin a sale by manually evaluating a subject's skin color. The salesperson then adjusts existing finished foundations so as to match the evaluated skin color. There are many disadvantages in manual blending. On many occasions there is a poor skin match, reproducibility is poor and extensive training is required of the salesperson. Additionally, the process is a cosmetic one which is embarrassing to patients unaccustomed to either buying cosmetics or who feel exposed at a public sales counter.

U.S. Pat. No. 4,871,262 (Krauss et al.) describes an automatic cosmetic dispensing system for blending selected additives into a cosmetic base. The system is intended for use at a retail establishment. A similar system is described in German Patent 41 10 299 C1 (Erdtmann), with the further element of a facial sensor. Although the aforementioned systems have advanced the cosmetic art, they are woefully lacking in addressing the needs of a person wishing to purchase a cosmetic skin product in a private setting.

U.S. Pat. No. 5,622,692 (Rigg et al.) reports on a method and apparatus for customizing a facial foundation product at the point of sale to a customer. A skin analyzer is applied to a customer's face for reading skin properties. A programmable device then receives the reading and correlates same with an optimal formula. A formulation machine then prepares a facial foundation product based upon instructions received about the optimal formula. Chemicals are then dosed and blended together from a series of dispensers each containing a monochromatic color composition. The optimal formula may be altered through customer preferences by manual alteration of the selected optimal formula. A problem with this method is its failure to compensate for non-normal areas of the skin. The method only focuses upon exact matching of color in the normal areas.

Accordingly it is an object of the present invention to provide a method for matching the skin properties of a person with a particular optimum formula in a private setting, such as a doctor's office, customer's home, hospital clinic, customer's office, etc.

Another object of the present invention is to provide a method for matching the skin properties of a person in a remote location with an optimal cosmetic formula manufactured in a separate central location away from the point of skin measurement in a manner that is both accurate and repeatable.

A further object of the present invention is to provide a method for matching the skin properties of a person with an optimal cosmetic formula in a central location that requires only minimal training of the color advisor in selecting the proper product.

These and other objects of the present invention will become more readily apparent through consideration of the following summary and detailed description which follow.

SUMMARY OF THE INVENTION

A method is provided for supplying a customized skin foundation product to a customer for covering skin imperfections, the method including:

(a) spectophotometrically measuring a customer's normal skin to obtain normal skin coloration values of lightness, redness and yellowness respectively denoted by L, a and b units;

(b) converting through calculation the normal skin coloration value to a modified value determined by a set program correcting L, a and b units; and (c) formulating a facial foundation having color based on the modified value.

The set program of the present invention has been obtained by studies matching patients with many types of skin imperfections to their appropriately colored foundation. Adjustments have been calculated for red and yellow imperfections.

Yellowness requires adjustment in the "a" unit of the normal skin coloration values according to the following schedule:
where b/a is no greater than 1.5, then from −0.5 to 2.5 a units are added, but preferably zero a units are added;

b/a is greater than 1.5 to 1.8, then from −0.5 to 3.0 a units are added, but preferably 0.25 a units are added;

b/a is greater than 1.8 to 2.1, then from 0 to 3.5 a units are added, but preferably 0.5 a units are added; and b/a is greater than 2.1, then from 0 to 4.0 a units are added, but preferably 1.25 a units are added.

Redness requires adjustment in the "b" unit of the normal skin coloration values according to the further following schedule:
where b/a is at least 1.5, then from −0.5 to 4.0 b units are added, but preferably one b unit is added;

b/a is 1.3 to less than 1.5, then from −0.5 to 4.5 b units are added, but preferably 1.5 b units are added;

b/a is 0.9 to less than 1.3, then from 0 to 5.0 b units are added, but preferably two b units are added; and b/a is less than 0.9, then from 0 to 5.5 b units are added, but preferably three b units are added.

Sometimes a customer may not be fully pleased with the calculated optimal formula of modified value. In this instance, a further modification is performed to enhance redness, pinkness, yellowness, lightness or darkness but all within the context of a preset customer preference program. L, a and b modified values are further revised based on numbers found from the clinical group studies.

Besides color, consideration must also be given to coverage. The term "coverage" means the percent of pigment within a foundation product. Coverage is determined by the type of skin condition to be hidden. For instance, rosacea needs (level 2 coverage) less than a birthmark (level 3 coverage). Thus the method further provides the optional step of determining the skin imperfection type and adjusting coverage of the foundation to insure the imperfection remains hidden.

The measuring device for the method may be a spectrophotomer/colorimeter having a visible light source, such as light emitting diodes (LED), xenon-arc, tungsten-halogen, etc. in the wavelength range of 400–900 nm. The visible light source may form the sensor portion of the spectro-photomer/colorimeter. Both visible and infrared wavelength light may be utilized in connection with the sensor portion.

The method prior to step (b) further provides a step of transmitting the normal skin coloration values and information on the type of skin imperfection as signals over a cable or as written on paper to a central monitoring location. Typical cables include telephone, facsimile and internet. Mail or courier may be employed instead of any electronic transmission.

The formulating step may be performed manually or optionally through a machine which includes:

(i) a mechanism for receiving information on the normal skin coloration values modified by correction of L, a and b values and for converting the modified information into a set of operating instructions;

(ii) a set of four dispensers, each of the four dispensers containing a different color chemical composition, the chemical compositions being colored respectively as a red, yellow, black and white monochrome composition;

(iii) a mechanism for activating dosing to a common dosing chamber of certain of the colored chemical compositions and at certain concentrations as determined by the set of operating instructions to form a dosed formula; and (iv) a mechanism for delivering the dosed formula into a container as a skin foundation product.

Delivery of the customized skin foundation product to a customer may either be by mail or a courier service.

Generally the formulating step will occur at the central monitoring location or at a site remote from the central monitoring location as well as remote from the measuring location. The term "remote" is meant to be any location further than 500 meters away, usually at distances over 10 kilometers.

Besides skin coloration, a variety of other skin characteristics may be measured. These include moisturization, oiliness, texture, irritation sensitivity, skin tone and markers of skin health such as radiance, skin damage, or age such as age spots.

Advantageously, at least some of the colored chemical compositions will include further skin benefiting ingredients such as emollients, sunscreens, moisturizers, perfumes, solvents, anti-wrinkling agents, skin-aging inhibitors, anti-acne, oil control agents, skin lighteners, antiseptics and antibiotics. Alternatively, these ingredients may be dosed via compositions separate from the colored chemical compositions, kept in separate dispensers.

An identification mark may be assigned to each customized facial foundation product. The mark may be labeled on the container. It may also be stored as information within a computer and permanently identified with the customer. An especially useful form of the mark is a bar code.

DETAILED DESCRIPTION OF THE INVENTION

A method has now been found which can provide a customized skin foundation product to cover skin imperfections. The system is particularly suitable for filling dermatologist prescriptions to cosmetically cover afflicted skin areas. Of course the method may have uses beyond cosmetic dermatology. It may be used to cover normal skin when a consumer wishes to lighten or darken their coloration to meet preconceived beauty shades.

The method begins by selection of an unafflicted area on a customer's neck/jawline typical of their general normal coloration. This area is cleaned preparatory to a reading. The spectrophotomer/colorimeter is then placed in proximity to the cleaned facial area. Visible light emitted in the 400–900 nm range by the device will be reflected off the skin surface and the reflected wavelength measured. A total of at least five skin readings along the neck/jaw line region will be taken. Total time for the reading will be approximately 30 seconds.

A first essential tool of the present invention is that of a skin analyzing module. The module is preferably a hand-held spectrophotometer/colorimeter operating with at least one visible light source such as LED, xenon-arc, tungsten-halogen, etc. Suitable skin analyzers are commercially available from Minolta Camera Co. Ltd, Japan (Minolta Spectrophotometer/Colorimeter CM-2002), from Colortec Associates, Accuracy Measurements and X-Rite. The module is preferably portable so that a customer's skin coloration may be measured at a location remote to a central monitoring location. Such remote locations include a physician's office, a customer's home, hospital, clinic or workplace.

The information obtained from the skin analyzing module at the customer's remote location is transmitted to a central monitoring site. Transmission may be performed via a telephone linkage, fax, postal service or any other conventional means known in the art.

Normal skin coloration value is reviewed either manually or, more preferably, by computer program to modify L, a and b with respect to the "base" corrections listed under Table I. The preferred corrections values are listed under the "base" column. However, the invention is also operative over a broader range of corrections as noted under the Summary of the Invention.

For example, an L, a, b reading of 65/15/15 is modified as follows. The L value is reduced by 1.0 units. Since the ratio of b/a is 1, the base correction for a is 0. Likewise, the ratio of b/a of 1 requires correction for b of 2.0 units. Thus the modified Lab value would be 64/15/17.

For a second example, an L, a, b reading of ;70/10/13 is modified as follows. The L value is reduced by 1.0 units.

Since the ratio of b/a is 1.3, the correction for a and b would respectively be 0 and 1.5 units. Thus, the modified Lab value would be 69/10/14.5.

TABLE I

Color Correction Chart

| | | CUSTOMER PREFERENCES | | | | | | | | | |
|---|---|---|---|---|---|---|---|---|---|---|---|
| Color | Base | More Red | | More Pink | | Lighter | | Darker | | More Yellow | |
| Range | (None) | +1 | +2 | +1 | +2 | +1 | +2 | +1 | +2 | +1 | +2 |
| L | −1.0 | −1.0 | −1.0 | 0.0 | 1.0 | 0 | 1.0 | −2.5 | −4.0 | −1.0 | −1.0 |
| a | | | | | | | | | | | |
| b/a: is no greater than 1.5 | 0 | 0.5 | 1.0 | 0.5 | 1.0 | 0 | 0 | 0 | 0 | 0 | 0 |
| b/a: is greater than 1.5 to 1.8 | 0.25 | 0.75 | 1.25 | 1.25 | 1.25 | 0.25 | 0.25 | 0.25 | 0.25 | 0.25 | 0.25 |
| b/a: is greater than 1.8 to 2.1 | 0.5 | 1.0 | 1.5 | 1.0 | 1.50 | 1.25 | 1.25 | 1.25 | 1.25 | 1.25 | 1.25 |
| b/a: is greater than 2.1 | 1.25 | 1.75 | 2.25 | 1.75 | 2.25 | 1.25 | 1.25 | 1.25 | 1.25 | 1.25 | 1.25 |
| b | | | | | | | | | | | |
| b/a is at least 1.5 | 1.0 | 1.0 | 1.0 | 1.0 | 1.0 | 1.0 | 1.0 | 1.0 | 1.0 | 2.0 | 3.0 |
| b/a is 1.3 to less than 1.5 | 1.5 | 1.5 | 1.5 | 1.5 | 1.5 | 1.5 | 1.5 | 1.5 | 1.5 | 2.5 | 3.0 |
| b/a is 0.9 to less than 1.3 | 2.0 | 2.0 | 2.0 | 2.0 | 2.0 | 2.0 | 2.0 | 2.0 | 2.0 | 3.0 | 4.0 |
| b/a is less than 0.9 | 3.0 | 3.0 | 3.0 | 3.0 | 3.0 | 3.0 | 3.0 | 3.0 | 3.0 | 4.0 | 5.0 |

Colors are the amount (in Lab Units) to apply for each situation (absolute, not relative to each other)
Each b/a value will be calculated from the default (b/a is at least 1.5) value
When multiple selected: Average is taken.

Table I further includes corrections for "customer preferences". If the facial foundation formulated through the base correction modified L, a, b color proves unsatisfactory to a customer, further adjustments may be made. For instance, the customer with measured L, a, b of 65/15/15 may prefer a very slightly yellower shade. The b/a ratio is 1. Thus, the measured L will be decreased by 1.0 units, a will be increased by zero units and b will be increased by 3.0 units. As another example, the same customer may have a preference for a much darker color shade. In this instance, the original L will be reduced by the −4.0 units, a remains unchanged and b will increase by 2.0 units.

Besides the spectrophotometer/colorimeter measurement, a trained facilitator such as a dermatologist conducts an independent determination of the skin imperfection by type. The skin condition types include: acne, rosacea, vitiligo, birthmarlks, nevi, keratosis, hyperpigmentation, melasma, spider veins, telangiectasia, acid peels, scars, portwine stains, laser resurfacing, every day complexion problems, psoriasis and any other unusual conditions.

The overall amount of pigments added is determined from an imperfection coverage decision tree as set forth in Table II. Mild skin imperfections such as acne, rosacea, keratosis and the like will receive a Coverage 2. More serious imperfections such as vitiligo, birthmarks, nevi, scars and portwine stains require the higher Coverage 3. Amounts of formula monochrome (color) and modifier compositions to achieve Coverages 1 to 3 are reported in Table III. The term "modifier" refers to a transluscent emulsion with talc. Modifier compositions have essentially identical components to that of the formula monochrome but without the color pigments.

TABLE II

Dermatology Coverage Decision Tree

| SKIN CONDITION | COVERAGE 1 | COVERAGE 2 | COVERAGE 3 |
|---|---|---|---|
| Acne | | X | |
| Rosacea | | X | |
| Vitiligo | | | X |
| Birthmarks | | | X |
| Nevi | | | X |
| Keratosis | | X | |
| Hyperpigmentation | | X | |
| Melasma | | X | |
| Spider Veins | | X | |
| Telangiectasia | | X | |
| Acid Peels | | X | |
| Scar | | | X |
| Portwine Stains | | | X |
| Laser Resurfacing | | X | |
| Everyday Complexion | X | | |
| Psoriasis | | X | |
| Other | | X | |

TABLE III

Color Additive Levels

| MAKE-UP VARIABLES | FORMULA MONOCHROMES | COVERAGE MODIFIER |
|---|---|---|
| Full Coverage 3 | 100.00% | 0.00% |
| Full Coverage 2 | 77.00% | 23.00% |
| Full Coverage 1 | 65.00% | 35.00% |

Formulation of the customized skin foundation products may be done manually or more advantageously can be accomplished through a formulation machine.

A typical formulation machine may include a series of dispensers, each containing a different cosmetic chemical composition. Each of the dispensers may be connected into a common dosing chamber through respective tubing. An electronic control board may also be part of the machine. This board may receive electronic instructions as to the optimal formula necessary to be dispensed. Servomechanical activators may be present within the machine to operate discharge valves for the respective dispensers. In accordance with the selected optimal formula, the requisite valves may be opened and the length of opening time may be regulated pursuant to the required quantity of any particular cosmetic chemical composition to be dispensed. Advantageously, a dosing chamber for receiving the compositions may be in the form of a dispensing container provided directly to the customer and serving as the product's package. The package may be disposable or designed for multiple use. The machine may also be capable of adjusting sample sizes of the dosed-mixed optimal formula.

A marking mechanism may be associated with the apparatus, preferably housed together with the formulation machine. The marking mechanism may utilize any numerical scheme, e.g. a customer's name, Social Security number, and/or other personalized identification, for connection with the optimal cosmetic product selected through the skin measuring process. Advantageously, the marking will be in the form of a bar code symbol.

When a particular facial foundation is required, an optimal color shade is delivered by combining a mixture of monochromatic compositions each of which is dosed from a respective dispenser. These dispensers contain a cosmetic chemical composition exhibiting one of four monochromatic colors, i.e. Red 16, Yellow 18, Black 20 and White 22. These colors will typically be achieved by incorporation of a respective iron oxide pigment (e.g. red iron oxide, yellow iron oxide or black iron oxide). White can be obtained from titanium dioxide.

The foregoing description illustrates selected embodiments of the present invention and in light thereof variations and modifications will be suggested to one skilled in the art, all of which are within the spirit and purview of this invention.

What is claimed is:

1. A method for providing a customized skin foundation product to cover skin imperfections, comprising:
   (a) spectophotometrically measuring a customer's normal skin to obtain normal skin coloration values of lightness, redness and yellowness respectively denoted by L, a and b units;
   (b) converting through calculation the normal skin coloration value to a modified value determined by a set program correcting L, a and b units; and
   (c) formulating a facial foundation having color based on the modified value.

2. The method according to claim 1 wherein the a unit of the normal skin coloration value is adjusted according to the following schedule:
where
   b/a is no greater than 1.5, then from −0.5 to 2.5 a units are added;
   b/a is greater than 1.5 to 1.8, then from −0.5 to 3.0 a units are added;
   b/a is greater than 1.8 to 2.1, then from 0 to 3.5 a units are added; and
   b/a is greater than 2.1, then from 0 to 4.0 a units are added.

3. The method according to claim 1 wherein the a unit of the normal skin coloration value is adjusted according to the following schedule:
where
   b/a is no greater than 1.5, then zero a units are added;
   b/a is greater than 1.5 to 1.8, then 0.25 a units are added;
   b/a is greater than 1.8 to 2.1, then 0.5 a units are added; and
   b/a is greater than 2.1, then 1.25 a units are added.

4. The method according to claim 1 wherein the b unit of the normal skin coloration value is adjusted according to the following schedule:
where
   b/a is at least 1.5, then from −0.5 to 4.0 b unit is added;
   b/a is 1.3 to less than 1.5, then from −0.5 to 4.5 b units are added;
   b/a is 0.9 to less than 1.3, then from 0 to 5.0 b units are added; and
   b/a is less than 0.9, then from 0 to 5.5 b units are added.

5. The method according to claim 1 wherein the b unit of the normal skin coloration value is adjusted according to the following schedule:
where
   b/c is at least 1.5, then one b unit is added;
   b/a is 1.3 to less than 1.5, then 1.5 b units are added;
   b/a is 0.9 to less than 1.3, then two b units are added; and
   b/a is less than 0.9, then three b units are added.

6. The method according to claim 1 comprising prior to step (b) a further step of transmitting the normal skin coloration value and skin imperfection type as signals over a cable or as written on paper to a central monitoring location.

7. The method according to claim 6 wherein the formulating of the facial foundation occurs at the central monitoring location or at a site remote from the central monitoring location and remote from a location where the measuring step was conducted.

8. The method according to claim 1 wherein formulating is performed by a machine comprising:
   (i) a mechanism for receiving information on the normal skin coloration values modified by correction of L, a and b values and for converting the modified information into a set of operating instructions;
   (ii) a set of four dispensers, each of the four dispensers containing a different color chemical composition, the chemical compositions being colored respectively as a red, yellow, black and white monochrome composition;
   (iii) a mechanism for activating dosing to a common dosing chamber of certain of the colored chemical compositions and at certain concentrations as determined by the set of operating instructions to form a dosed formula; and
   (iv) a mechanism for delivering the dosed formula into a container as a skin foundation product.

9. The method according to claim 1 wherein the measuring is performed with at least one visible light source having a wavelength in the range of 400–900 nm.

10. The method according to claim 1 wherein measuring includes evaluating at least one skin characteristic other than coloration selected from the group consisting of a customer's skin moisturization, oiliness, texture, irritation, sensitivity, skin tone, aging markers and combinations thereof.

11. The method according to claim 8 wherein the chemical compositions include ingredients selected from the group consisting of emollients, sunscreens, moisturizers, perfumes, solvents, wrinkling and skin-aging inhibitors and medicines, oil control agents, anti-acne agents, skin whitening actives, antiseptics, antibiotics, anti-inflammatory agents and combinations thereof.

12. The method according to claim 1 further comprising the step of modifiying the normal skin coloration values by consideration of a customer's color preference requests.

13. The method according to claim 1 further comprising the step of assigning an identification mark to each customized facial foundation product, labeling the mark on a container for the product, and also storing the identification mark to permanently identify the customized facial foundation product with the customer.

14. The method according to claim 13 wherein the mark is a bar code.

* * * * *